United States Patent [19]
Beaty et al.

[11] Patent Number: 5,674,071
[45] Date of Patent: *Oct. 7, 1997

[54] DENTAL LABORATORY COMPONENTS AND PROCEDURES FOR ANATOMICAL RESTORATION ON ARTIFICIAL ROOT FIXTURES

[76] Inventors: Keith D. Beaty, 245 Miramar Way, West Palm Beach, Fla. 33405; Curtis E. Jansen, 712 Sandpiper Way, North Palm Beach, Fla. 33408

[*] Notice: The term of this patent shall not exend beyond the expiration date of Pat. No. 5,338,196.

[21] Appl. No.: 527,508

[22] Filed: Sep. 13, 1995

Related U.S. Application Data

[63] Continuation of Ser. No. 248,497, May 24, 1994, abandoned, which is a continuation of Ser. No. 43,928, Apr. 8, 1993, Pat. No. 5,338,196.

[51] Int. Cl.$^6$ .............................................. A61C 8/00
[52] U.S. Cl. ..................... 433/172; 433/173; 433/214
[58] Field of Search ............................... 433/172, 173, 433/174, 175, 214

[56] References Cited

U.S. PATENT DOCUMENTS

| | | | |
|---|---|---|---|
| 4,758,161 | 7/1988 | Niznick | 433/173 |
| 4,850,870 | 7/1989 | Lazzara et al. | 433/174 |
| 4,850,873 | 7/1989 | Lazzara et al. | 433/220 |
| 4,856,994 | 8/1989 | Lazzara et al. | 433/173 |
| 4,955,811 | 9/1990 | Lazzara et al. | 433/173 |
| 4,988,298 | 1/1991 | Lazzara et al. | 433/173 |
| 5,006,069 | 4/1991 | Lazzara et al. | 433/173 |
| 5,015,186 | 5/1991 | Detsch | 433/173 |
| 5,030,096 | 7/1991 | Hurson et al. | 433/173 |
| 5,035,619 | 7/1991 | Daftary | 433/173 |
| 5,040,983 | 8/1991 | Binon | 433/173 |
| 5,071,351 | 12/1991 | Green, Jr. et al. | 433/173 |
| 5,073,111 | 12/1991 | Daftary | 433/173 |
| 5,100,323 | 3/1992 | Friedman et al. | 433/173 |
| 5,145,371 | 9/1992 | Jorneus | 433/173 |
| 5,145,372 | 9/1992 | Daftary et al. | 433/173 |
| 5,188,800 | 2/1993 | Green, Jr. et al. | |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,281,140 | 1/1994 | Niznick | 433/173 |
| 5,292,252 | 3/1994 | Nickerson et al. | 433/173 |
| 5,297,963 | 3/1994 | Daftary | 433/172 |
| 5,334,024 | 8/1994 | Niznick | 433/173 |
| 5,431,567 | 7/1995 | Daftary | 433/172 |

OTHER PUBLICATIONS

Exhibit A, a drawing of a healing abutment.
Exhibit B, an assembly drawing of a coping and the component drawings which comprise the coping assembly.
*Single Tooth Implants*, George Perri, DS, et al., CDA Journal, vol. 17, No. 3, Mar. 1989.
Lewis, S.G. et al. Single Tooth Implant Supported Restorations. *Intnatl. Jrnl. of Oral & Maxillofacial Implants.* vol. 3, No. 1, pp. 25–30, 1988.
Lewis, S.G. et al. The "UCLA" Abutment, *Intnatl. Jrnl. of Oral & Maxillofacial Implants* 1988 vol. 3, No. 3 pp. 183–189, 1988.

*Primary Examiner*—Cary E. O'Connor

[57] ABSTRACT

A second stage healing abutment for forming and preserving in the mucosa above a dental implant a transmucosal opening large enough to receive an artificial tooth that faithfully replicates a natural tooth being restored, and a companion transfer coping having identical transmucosal portions for forming in a laboratory model a faithful replica of the transmucosal opening in which to fabricate the artificial tooth, and methods of using the same.

85 Claims, 2 Drawing Sheets

DENTAL LABORATORY COMPONENTS AND PROCEDURES FOR ANATOMICAL RESTORATION ON ARTIFICIAL ROOT FIXTURES

This application is a file wrapper continuation of application Ser. No. 08/248,497, filed May 24, 1994, now abandoned, which is a continuation of application Ser. No. 08/043,928 filed Apr. 8, 1993 and issued as U.S. Pat. No. 5,338,196 on Aug. 16, 1994.

BACKGROUND OF THE INVENTION

The field of restorative dentistry using artificial roots in the presently preferred form of osseointegrated cylinder shaped dental implants has progressed to the level where attention is now being given to providing restorations on them that closely replicate natural dentition in appearance, especially where the teeth emerge from the gums. The problems of achieving a natural locking emergence profile are addressed using a technique for fabricating implant supported restorations directly to an implant, employing custom wax patterns fashioned on abutment cylinders to achieve, for example, a custom made porcelain fused to metal restoration. This technique is described in published articles that appeared in The International Journal of Oral & Maxillofacial Implants, Vol. 3, Number 1, 1988 at pages 25–26 "Single Tooth Implant Supported Restorations" Lewis, S. G. et al., and Number 3, 1988 at pages 183–189 "The 'UCLA' Abutment", Lewis, S. G. et al. A similar result using a different abutment is described in U.S. Pat. No. 4,988,298, which is owned by the Assignee of the present invention. The problem is incompletely addressed in U.S. Pat. No. 5,073,111 issued to Daftary Dec. 17, 1991.

The dental restoration of a wholly or partially edentulous patient with dentition supported on dental implants is now frequently done in two stages. In the first stage the implant is placed and left to integrate with the jawbone. The second stage begins with re-accessing the implant through the gum and maintaining access with a healing cap or the like, and continues through the fabrication of restorative dentition in the laboratory using measurements and other information taken from time to time from the patient. During that time the patient may have only a healing cap in his or her mouth, or according to more recent and sophisticated procedures the patient may be fitted with temporary dentition from which additional refining measurements can be taken. Nevertheless, the healing abutments and the transfer copings, or pick up copings, of the prior art do not cooperate to provide room for making and installing on the implant an artificial tooth having an aesthetically pleasing or anatomically correct emergence profile. The gingival aspect of an implant is, typically not more than about 4.1 mm in diameter, whereas the longer (mesial-distal) dimension of a natural tooth where it emerges from the gum is between about 4.5 mm and about 8.0 mm. According to present practice, healing abutments, which are cylindrical in cross section, are chosen to approximate the mesial-distal dimension of the tooth being replaced. At the same time, the transfer copings, or pick up copings, of the prior art are all one size, about 4.5 mm in diameter. As a result, a gap is left in the gingiva, around the coping, and impression material fills this gap when an impression is taken. The gingiva also tend to collapse into this gap, resulting in less than accurate replication of the conditions in the patient's mouth. As a further consequence of these problems, it is difficult to make soft tissue models accurately. Stone models replicate these errors, and this requires technicians to shape the stone manually to comply with the conditions in the patient's mouth, or risk producing a crown with an inaccurate emergence profile or crown to abutment margin that is misplaced. These are severe problems, resulting from the fact that the designers of prior art components have thus far failed to recognize them. The present invention teaches new surgical and laboratory components, and new procedures, which eliminate such inaccurate and time wasting procedures, and improve the art of making anatomically correct and aesthetically pleasing dental restoration.

GENERAL NATURE OF THE INVENTION

In accordance with the present invention, a healing cap or healing abutment sized to maintain space for a desired emergence profile through the gum is used at the beginning of the second stage, in combination with an impression coping, or a pick up coping, having similar size specifications so that when the impression coping is fitted to the implant for taking the impression from which the stone model will be made the space for the desired emergence profile established in the gum by the healing abutment, or cap, will be preserved and replicated in the stone model, and in a soft tissue model, if desired. From such models restorative dentition can be fabricated without requiring the use of a specially contoured tooth support abutment as taught by Daftary, for example. Rather, artificial teeth replicating in all material respects the natural teeth that they replace can be fashioned on the model using components that have become standard in the art.

In one of its aspects the invention teaches a new method of preparing an aesthetically pleasing, as well as anatomically correct dental restoration on a natural or artificial root comprising first the step of preparing in the gingiva overlying the root an opening to the gingival aspect of the root, which opening is sufficient to accommodate the shape and contour of a natural tooth emerging through the gingiva from the root, followed by the step of making a rigid (e.g., stone) model that reproduces in stone or in overlying soft tissue exactly that opening and gingival aspect of the root, and then the step of forming on the model an artificial tooth that replicates in that opening the shape, size and contours desired in the restoration, and finally installing that restoration on the root. In another aspect, the invention provides a healing member (sometimes called a cap) that has a transmucosal section having at one end the subgingival cross sectional size and shape of the artificial root and where it emerges from the gingiva the mesial-distal size of the natural tooth being replaced, and means to attach that healing member non-rotatively to the root, for establishing the above mentioned opening in the gingiva. In another aspect, the invention provides a transfer coping for use in making the above mentioned rigid model having a transmucosal section that is substantially identical in cross sectioned size and shape to the transmucosal section of the healing member so as to fit fully within the opening in the gingiva that was formed by the healing member, and a supragingival section shaped for non-rotational embedment in resilient modelling material, together with means to attach the coping non-rotatively to the root. In still another aspect, the invention provides sets of matched pairs of healing members and transfer copings shaped and sized for use according to the invention to prepare restorations of particular types of teeth, such as molars, premolars, bicuspids, and incisors, as examples.

These and other features of the invention will be explained in greater detail in the following description of certain exemplary embodiments of the invention referring to the accompanying drawings in which.

DETAILED DESCRIPTION OF THE DRAWINGS

Figure 1:
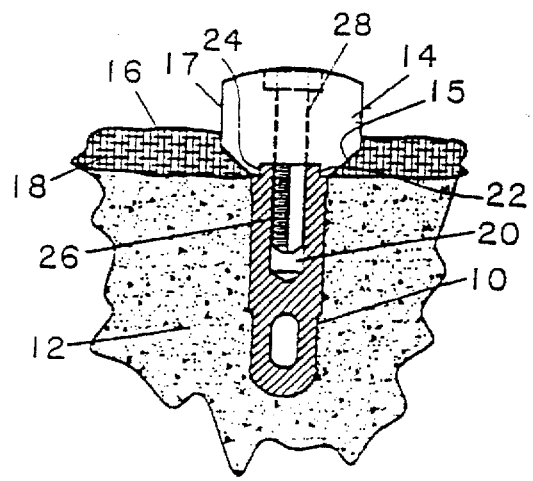
FIG. 1 is a longitudinal section that shows an implant installed in a bone with a healing cap in place.

FIG. 1 schematically illustrates a dental implant 10, of the osseointegrated type installed in a section of jawbone 12. The "second stage surgery" has begun, and a healing abutment 14 is in place on the implant. In order to provide for a more natural emergence profile in the final restoration, this abutment expands in a tapered transmucosal section 15 from the end contacting the implant toward an outer surface 16 of surrounding gingiva 18, beyond which walls 17 of the abutment extend vertically. As shown in FIG. 1, a portion of the vertical walls 17 is immersed in the gum tissue, below the outer surface 16, together with the tapered section 15. The implant has an internally threaded bore 20 axially located in it, surrounded at its gingival opening by a non-round boss 22, the external cross section of which typically is hexagonal. The healing abutment 14 has a corresponding non-round socket 24 enveloping the boss 22. In the illustrated embodiment through-bolt 26 passing through an axial bore 28 in the healing abutment is used to attach the abutment to the implant, in a well known manner. Attached in this manner, the healing abutment is not able to be rotated around the axis of the bolt. Healing abutments according to the invention may be prefabricated with a transmucosal section 15 having at the gingival surface 16 a round cross sectional shape the diameter of which is approximately equal to the mesial-distal dimension of the lost tooth being restored. Alternatively, the peripheral contour in the tapered section 15 may closely replicate the emergence profile of the natural tooth that was in the site where the implant 10 is installed. The invention contemplates providing sets of such prefabricated healing abutments, together with matching impression copings. The supragingival vertical walls of the healing abutment and the impression copings used with it may also be contoured to mimic the natural tooth cross-section, depending on the thickness of the gingiva 18 and the corresponding vertical dimension of the abutment.

Figure 2:
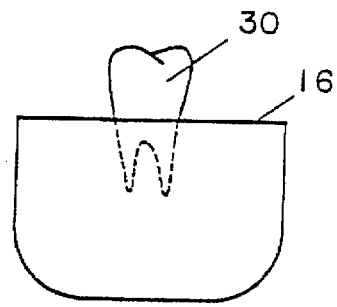
FIG. 2 shows a natural bicuspid.

FIG. 2 shows the general contours of a bicuspid 30 emerging from the outer surface 16 of the gingiva. A typical bicuspid is approximately 5.5 mm in mesial-distal dimension at the surface 16. A typical standard abutment or impression coping is at most 4.5 mm in diameter. Some teeth, e.g., molars, may be as much as 6.0 or 7.0 mm in mesial-distal dimension. Moreover, as appears in FIG. 6, which illustrates the cross section of an emergence profile 75 characteristic of an anterior tooth (not shown), it is also desirable to be able to provide for emergence profiles the cross sections of which do not even approximate round. To address these problems the invention provides methods and means to create and preserve openings in the gingiva 18 that are significantly larger than the cross section of the implant 10 and that may be round, or may have any desirable shape, and to preserve each such opening throughout the laboratory procedure for making and fitting the relevant dental restoration. Thus, as has been mentioned, the cross sectional shape of the transmucosal tapered portion 15 and the vertical wall portion 17 of the healing abutment may be round as long as its diameter approximates the mesial-distal size of the natural tooth.

Figure 3:
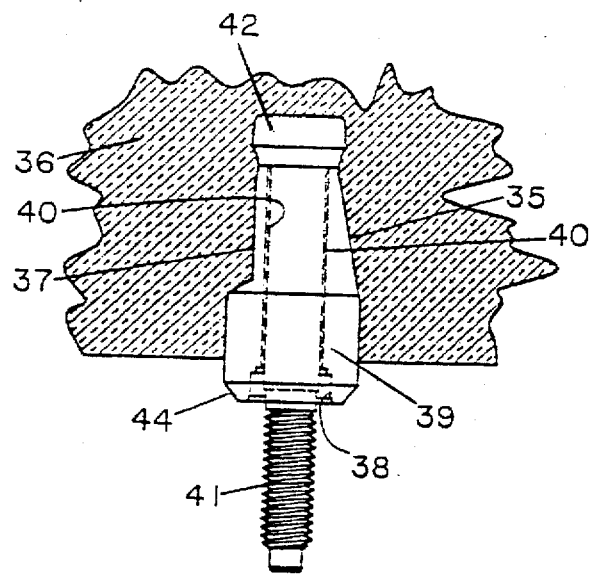
FIG. 3 is a longitudinal section that shows a transfer coping used to make an impression.

FIG. 3 shows a transfer coping 35 of a kind used to take impressions, buried in an impression material 36. The essential structure of this impression coping is described and claimed in U.S. Pat. No. 4,955,811, which is owned by the Assignee of the present invention. This impression coping has a flat surface 37 for locating it non-rotationally in the impression material, a hexagonal socket 38 in its base 39 for fixing it non-rotationally on the implant 10, an axial through bore 40 and a bolt 41 with an expanded head 42 for holding it in the impression material. The bolt 41 is used to attach the impression coping 35 to the implant 10. For the purposes of the present invention, the impression coping has a tapered section 44 at its end surrounding the socket 38 that replicates in size and shape the tapered transmucosal section 15 of the healing abutment 14. As shown in FIG. 3, a portion of the base 39 emerges from the impression material 36, together with the tapered section 44. The base 39 may also be contoured to mimic the natural cross section of the tooth being replaced, as its mentioned above.

Figure 4:
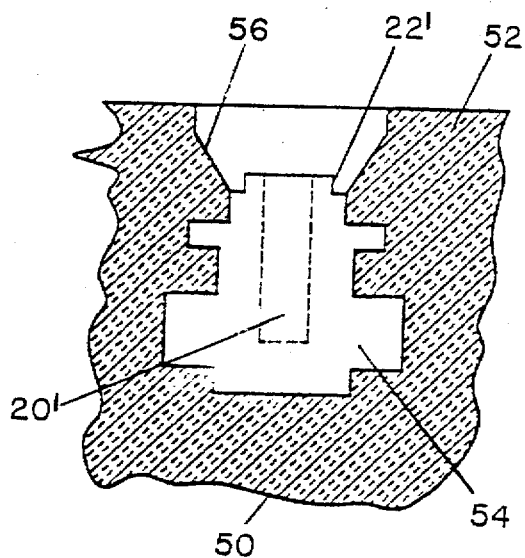
FIG. 4 is a longitudinal section that shows a stone model made from the impression.

FIG. 4 is a stone model 50 of the patient's implant installation site shown in FIG. 1. An implant replica 54 is encased in stone 52, according to well known dental laboratory practice. The replica 54 has a threaded bore 20' and a non-round boss 22' that are identical to the bore 20 and boss 22 of the implant 10. A tapered recess 56 in the surface of the stone surrounding the end of the replica 54 matches in size and shape the tapered section 44 and a part of the base 39 of the impression coping 35. Thus, the healing abutment fits equally well on the implant replica as on the implant.

The illustration in FIGS. 1, 3, and 4 of a process in which the openings in the gingiva 18 and the model 50 have a "vertical" portion as well as the tapered portion is exemplary only, and is not intended to limit the invention to that feature.

Figure 5:
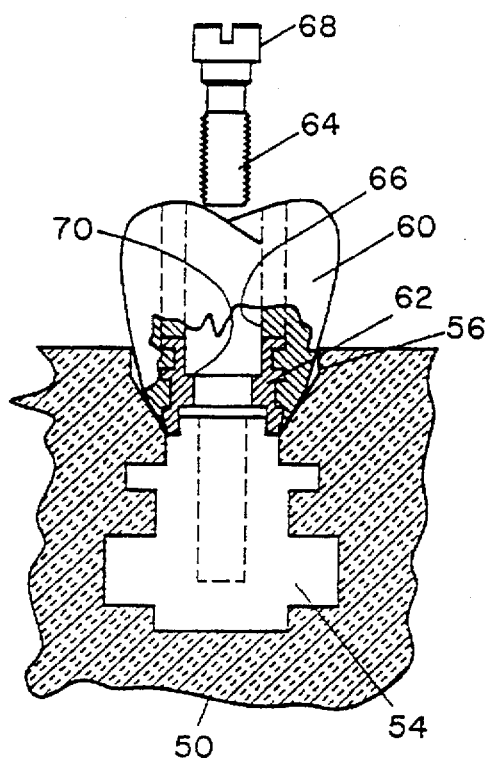
FIG. 5 shows the invention as used to replicate the natural tooth of FIG. 2.

An artificial bicuspid 60, as shown in FIG. 5, can be made with the aid of the model 50. A known form of core 62 is non-rotatively attachable to the implant replica with a screw bolt 64, passed through a through-bore 66 in the core. Head 68 of the bolt comes to rest on a shoulder 70 in the core 62, holding the core firmly attached to the implant replica 54 within the tapered recess 56. The artificial tooth is fashioned on the core using any available dental material, such as porcelain or acrylic, for example. The dental material extends well within the tapered recess 56, so that outside this recess the core material cannot be seen. The core itself can be made of any suitable rigid material, such as titanium and its dilute alloys. After being fashioned and anatomically shaped as desired, the artificial tooth 60 can be transferred to the implant 10 and its appearance will be as is shown in FIG. 2. It will emerge from the gingiva 18 looking exactly the same as a natural tooth. According to well known dental practice, the opening into the core at the top of the tooth 60 will be filled with a suitable dental cement or the like, and polished so as to be for all practical purposes not distinguishable from the rest of the tooth. The above mentioned U.S. Pat. No. 4,988,298 illustrates an artificial tooth that can benefit from the invention.

Figure 6:
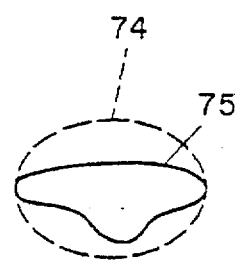
FIG. 6 shows the cross section of a natural emergence profile that the invention can replicate.

Because the component parts used in this invention can be made so that they are non-rotatably attachable together, it is not necessary that they be cylindrical in cross section where they are attachable one to the other. Thus, the healing abutment 14, the base 39 of the impression coping 35, and the subgingival section of the artificial tooth 60 can each be given the same cross sectional size and shape, changing gradually from round at the subgingival aspect of the implant fixture 10 to non-round proceeding toward the gingival surface through which the artificial tooth will emerge from the surface 16 of the overlying gingiva. In this manner that size and shape can initially be established by the healing abutment in the opening through the gingiva 18, and the same size and shape in the correct orientation around the axis of the implant 10 can be replicated and preserved in the model 50, thereby enabling the tooth 60 to be formed in the laboratory with the correct emergence profile. This feature of the invention is particularly advantageous when restoring anterior dentition, where the emergence cross section, e.g., 75 as is indicated in FIG. 6, has segments that are almost straight, and curved segments that turn on short radii.

The invention is not limited to the use of non-rotatively attachable components. In its more general aspects, the invention contemplates providing transmucosal openings that may be round with a diameter that approximates the mesial-distal dimension of the missing tooth that is being replaced, and preserving that dimension in a round opening throughout the laboratory procedure. This simple arrangement provides the basic advantages of the invention, which include eliminating the need to surgically expand a trans-tissue opening that was originally, or has become, too small to receive the restoration, and eliminating the need for laboratory technicians to hand finish stone models in which the trans-tissue opening was incorrectly formed due to causes that are mentioned above. Provided the trans-tissue opening is formed and maintained large enough to receive the restoration, last minute surgery is not needed, and the tissue will grow to the restoration. Referring to FIG. 6, dashed line circle 74 represents a trans-tissue opening that is larger then the tooth 75. In this situation, there is no need to provide the non-rotative features such as the mating non-round boss 22 and socket 24.

According to the invention, healing abutments 14 and transfer copings 35 may be prefabricated in sets of pairs, each pair having an "emergence profile contour" that is representative of a range of teeth of a particular type; that is, for example, large molars, small molars, premolars, bicuspids, and anterior incisors. The restorative dentist may then choose a pair that most closely replicates the emergence profile that is desired, modify the members of that pair if such is deemed necessary or desirable, and then make a restoration in accordance with the present invention that will be aesthetically pleasing and very close to anatomically correct.

Figure 7:
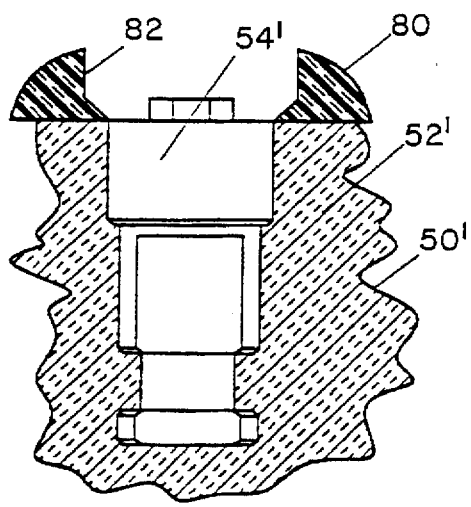
FIG. 7 is a cross section that shows a soft tissue model.

FIG. 7 shows a stone model 50' similar to the model 50 of FIG. 4, but in cross section rather than in longitudinal section, and including a stone foundation 52' rigidly holding an implant replica 54'. A soft tissue layer 80, which replicates the human gingiva 18, overlies the stone part. This layer can be made of any suitable plastics or rubber-like material having physical properties such as softness and elasticity that resemble the physical properties of human gum tissue. Certain silicone based rubber and plastics materials are suitable, preference being given to those that can be fabricated from a soft flowable state. In use, the soft flowable plastics material is placed in the impression around the tapered section 44 and emerging portion of the base 39 of the transfer coping 35 to a thickness the same as that of the patient's gingiva 18. The resulting opening 82 is similar to the opening 56 in the stone that is shown in FIG. 4. It has the advantage that the laboratory technician can manipulate the model exactly as the dentist manipulates the patient's gingiva.

Figure 8:
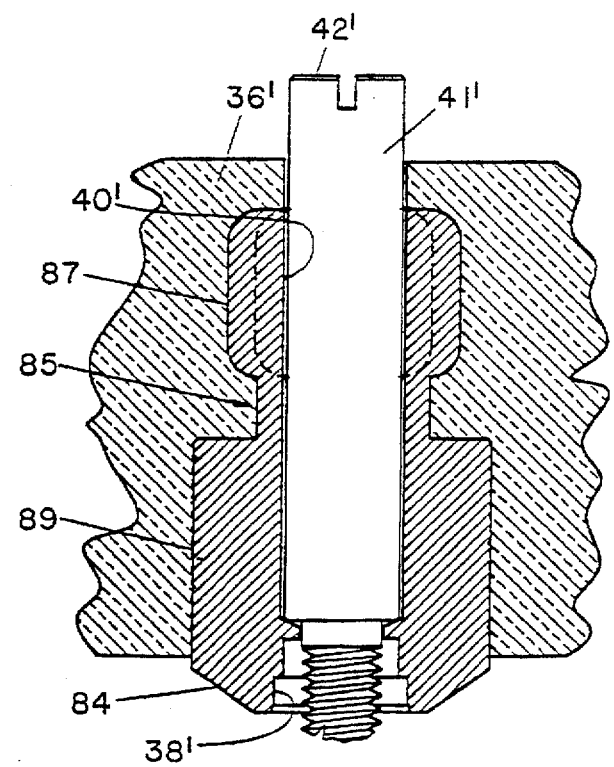
FIG. 8 shows a pick up coping used to make an impression.

FIG. 8 shows a pick-up coping 85 buried in an impression material 36'. This impression coping has a non-round head portion 87 for anchoring the coping non-rotationally on the implant, if desired, an axial through bore 40' and a bolt 41' passing through this bore to attach the impression coping to the implant. The proximal end 42' of the bolt has no expanded head on it for the reason that in use when an impression is taken, this end of the bolt extends through a hole in the impression tray (not shown) and, when the impression material has set up in the tray the bolt 41' is unscrewed from the implant by accessing its proximal end 42' from the outside, the tray and the coping 85 remains in (is "picked up" by) the impression material, being anchored therein by its expanded head 87. For the purposes of this invention, the pick up coping 85 functions like the transfer coping 35 of FIG. 3. Thus, the base 89 is expanded to a diameter that approximates the mesial-distal dimension of the natural tooth that is being restored and tapered section 84 reduces subgingivally to the diameter of the implant or other underlying support that may be present. Like the base 39 in FIG. 3, the base 89 may be contoured to mimic the cross section of the natural tooth.

We claim:

1. A method of preparing an artificial tooth for placement on a natural or artificial root means with an overlying gingiva layer having an opening to the root means, which comprises:

forming the gingiva opening to the root means with a healing member attached to said root means and expanding therefrom to a substantially wider diameter substantially replicating the width of the natural tooth where the natural tooth emerged from the gingiva at the gingival surface;

making a model of the gingiva opening to the root means from an impression using a transfer coping attached to said root means and having substantially the same dimensions and contours as said healing member in said opening and thereby substantially replicating in the model the gingiva opening to the root means;

forming the artificial tooth in the replicated gingiva opening on the model; and installing the artificial tooth to the root means through said gingiva opening.

2. The method of claim 1 wherein the diameter of the gingiva layer opening to the root means has a substantially similar diameter to that of the root means and the dimension changes to a larger diameter as it proceeds through the gingiva from the root means to the gingival surface.

3. The method of claim 2 wherein the diameter of the gingiva layer opening at the gingival surface is substantially similar to the width of the natural tooth where the natural tooth emerged from the gingiva.

4. The method of claim 1 wherein the healing member is tapered, having a smaller section adjacent to and having generally the size of the root means and a larger section having a diameter replicating the width of the natural tooth where the natural tooth emerged from the gingiva.

5. The method of claim 1 wherein the healing member has a first transmucosal section similar in size to the root means, the first transmucosal section enlarging in size to a second transmucosal section having a diameter replicating the width of the natural tooth where the natural tooth emerged from the gingiva.

6. The method of claim 1 wherein the making of the model further comprises:

making an impression of the transfer coping; and making the model from the impression with the transfer coping in the impression material.

7. A method of preparing an artificial tooth for placement on a natural or artificial root means with an overlying gingiva layer having an opening to the root means, said root means having a transverse dimension at its gingival end that is substantially smaller than the width of the natural tooth where the natural tooth emerged from the gingiva, which comprises:

fastening a healing member to the root means, the healing member having a diameter that replicates the width of the natural tooth where the natural tooth emerged from the gingiva;

allowing the gingiva opening to form to the healing member diameter;

removing the healing member from the root means;

fastening a transfer coping to the root means, the transfer coping replicating the healing member and the gingiva opening to the root means dimensions;

making an impression of the transfer coping and the surrounding gingiva area;

making a model from the impression with the transfer coping in the impression material replicating in the model the gingiva opening to the root means formed by the healing member;

forming the artificial tooth in said replicated opening on the model; and installing the artificial tooth to the root means.

8. A set of dental components for use with a dental root means fixed in a site with an overlying gingiva layer having an opening to the root means, said root means having a transverse dimension at its gingival end that is substantially smaller than the width of the natural tooth where the natural tooth emerged from the gingiva, said set comprising:

a plurality of generally round healing members each including a tapered portion with a smaller section having generally the diameter of the root means and a larger section having a size and contour for forming said opening in said gingiva, said larger section of at least one healing member having a different size than the remaining ones of said plurality of healing members;

means to attach one of said plurality of members to said root means;

a plurality of transfer components each having a portion with substantially the same size and contour as said larger section of a corresponding one of said plurality of healing members so as to fit fully into said opening in place of said corresponding one of said plurality of healing members, said portions of said plurality of transfer components having different sizes corresponding to the different sizes of said larger sections of said plurality of healing members; and means to attach one of said plurality of transfer components to said root means with said portion fitted into said opening.

9. A set of transfer components for use in fabricating a model of a patient's edentulous jawbone site containing a root means with an overlying gingiva layer having an opening to the root means, said root means having a transverse dimension at its gingival end that is substantially smaller than the width of the natural tooth where the natural tooth emerged from the gingiva, each transfer component of said set comprising:

a generally round transmucosal portion for extending through said opening and engaging said root means with a lower end that is substantially the same size as said transverse dimension of said root means, said transmucosal portion tapering from an intra-gingival diameter to a smaller diameter at said lower end, at least one of said transfer components of said set having a different intra-gingival diameter than the other ones of said transfer components for permitting the selection of a transfer component corresponding to the size of said opening;

an impression portion adjacent to the transmucosal portion for extending into impression material; and means for fastening one of the transfer components to the root means.

10. The set of transfer components according to claim 9 wherein at least one of said set of transfer components is a transfer coping.

11. The set of transfer components according to claim 9 wherein at least one of said set of transfer components is a pick-up coping.

12. A set of transfer components for use in fabricating a model of a patient's edentulous jawbone site containing a root means with an overlying gingiva layer having an opening to the root means, said root means having a transverse dimension at its gingival end that is substantially smaller than the width of the natural tooth where the natural tooth emerged from the gingiva, each transfer component of said set comprising:

a first transmucosal portion having a root means end similar in size to said transverse dimension of the root means;

a generally round second transmucosal portion being of a larger size than and adjacent to the first transmucosal portion;

an impression portion adjacent to the generally round second transmucosal portion for extending into impression material;

means for fastening the transfer coping to the root means;

the first transmucosal portion diverging from the root means end to the larger size of the second transmucosal portion;

the generally round second transmucosal portion of at least one of said transfer components of said set having a different size than the other ones of said transfer components for permitting the selection of a transfer component corresponding to the size of said opening.

13. The set of transfer components of claim 12 wherein at least one the transfer components further comprises an elongated body with a through bore between the root means end and the impression portion for passage of bolt means to attach the transfer component to the root means.

14. The set of transfer components of claim 13 wherein the cross sectional dimension of the transmucosal portion is substantially larger than any cross sectional dimension of the impression portion.

15. The set of transfer components according to claim 12 wherein at least one of said set of transfer components is a transfer coping.

16. The set of transfer components according to claim 12 wherein at least one of said set of transfer components is a pick-up coping.

17. A set of components for fabricating an artificial tooth replicating a natural tooth at a location having a root means with overlying gingiva layer having an opening to the root means, said root means having a transverse dimension at its gingival end that is substantially smaller than the width of the natural tooth where the natural tooth emerged from the gingiva, said set comprising:

a plurality of generally round healing members each having a tapered transmucosal portion with a smaller section and a larger section, the smaller section having generally the size of the root means and the larger section for forming and maintaining the opening in the gingiva and for gingival healing around the healing member to the desired shape and diameter, said larger section of at least one healing member having a different size than the remaining ones of said plurality of healing members;

means for fastening one of said plurality of healing members to the root means;

a plurality of transfer components each including a generally round transmucosal portion for extending through the gingiva opening to the root means and an impression portion adjacent to said transmucosal portion for extending into impression material, said transmucosal portions of said plurality of transfer components having different sizes corresponding to said larger sections of said plurality of healing members; and means for fastening one of said plurality of transfer components to the root means so that when the healing member is removed from the gingiva layer and the transfer component is fastened onto the root means the transfer component replicates the dimensions of the healing abutment in the gingiva opening to the root means for making an impression and a rigid model of the resulting gingiva opening to the root means formed by the healing member.

18. The set of components of claim 17 wherein the transmucosal portions of the transfer components taper to a smaller section generally the size of the root means.

19. The set of components of claim 17 wherein said transmucosal portions of the transfer components include:
a first transmucosal portion having a root means end similar in size to the root means; and
a generally round second transmucosal portion of larger size adjacent to the first transmucosal portion;
the generally round second transmucosal portions of said transfer components being said different sizes corresponding to said larger sections of said plurality healing members.

20. The set of components of claim 17 further comprising means for locking the healing member against turning relative to the root means and means for locking the transfer coping against turning relative to the root means.

21. The set of components of claim 17 wherein the transfer coping further comprises an elongated body with a through bore between the root means end and the impression material end for passage of bolt means to attach the transfer coping to the root means.

22. A method of preparing an anatomically correct dental restoration for installation on a natural or artificial root which includes means to attach said restoration to said root, said root means having a transverse dimension at its gingival end that is substantially smaller than the width of the natural tooth where the natural tooth emerged from the gingiva, comprising the steps of preparing in the gingiva overlying said root an opening to the gingival aspect of said root and said attaching means, said opening having at the gingival surface substantially the full cross-sectional size of a natural tooth emerging through said gingiva from said root, making a model of said gingiva replicating substantially identically said opening and said gingival aspect of said root including said attaching means, forming on the resulting replica of said root and said attaching means in said model an artificial tooth substantially replicating in said opening the emergence profile of said natural tooth, and installing said artificial tooth on said root.

23. A method according to claim 22 in which the cross-sectional dimension of said opening at said gingival aspect of said root is substantially similar to that of said root and said dimension gradually changes to a larger opening as it proceeds through said gingiva to said surface.

24. A method according to claim 22 in which the cross-sectional shape of said opening at the surface of said gingiva is substantially similar to the cross-sectional shape of said natural tooth at said surface.

25. A method according to claim 22 including the step of forming an initial opening in said gingiva, fixing to said root a component having a transmucosal part in said initial opening and a subgingival end confronting said root, the cross-section of said subgingival end being substantially similar in size and shape to the confronting cross-section of said root, the cross-section of said transmucosal part enlarging to substantially said full cross-sectional size where it emerges from said gingiva.

26. A method according to claim 25 in which said component is a healing member and said healing member is left in place on said root for a period of time in order to form said opening to said size and contour.

27. A method according to claim 26 including the further steps of removing said healing member from said root and substituting for it a transfer coping having a substantially similar transmucosal part, making a rotation-inhibiting impression of said coping and surrounding gingiva, and making said model from said impression with said coping in it.

28. A set of transfer components for use in making a model of a patient's edentulous jawbone site containing root means in the jawbone and an opening through the overlying mucosa exposing the gingival end of said root means, said root means having a transverse dimension at said exposed end that is substantially smaller than the width of the natural tooth where the natural tooth emerged from the gingiva, said opening having at one end substantially the cross-sectional size and shape of said exposed end of said root means and at its other end substantially the cross-sectional size of a natural tooth at said site where said tooth emerges through the surface of said mucosa, said root means including attaching means for receiving dental restorative means, each of said transfer components in said set comprising:

a non-round transmucosal section sized and shaped substantially to mate with the size and shape of said opening, the transmucosal section of at least one transfer component being a different shape than the remaining ones of said transfer components;

a supragingival section adapted for embedment in resilient modelling material; and means to connect a subgingival end of said transmucosal section to said attaching means of said root means within said opening.

29. A set of transfer components according to claim 28 in which the cross-section of said transmucosal section is substantially round at said subgingival end confronting said exposed end of said root means and changes gradually to non-round as it proceeds away from said subgingival end.

30. A set of transfer components according to claim 28 in which said transmucosal section includes portions which are nearly straight.

31. The set of transfer components according to claim 28 wherein at least one of said set of transfer components is a transfer coping.

32. The set of transfer components according to claim 28 wherein at least one of said set of transfer components is a pick-up coping.

33. A set of components for use in making an artificial tooth which emulates a natural tooth missing from a patient's jawbone site containing root means in said jawbone site, said root means having a transverse dimension at its gingival end that is substantially smaller than the width of the natural tooth where the natural tooth emerged from the gingiva, said root means including attaching means for attaching said artificial tooth thereto, said set comprising:

a plurality of healing members each having a first transmucosal section for establishing in the mucosa overlying said jawbone at said site an opening exposing the gingival end of said root means and said attaching means of said root means through said mucosa, said first transmucosal section being attachable at one end to said gingival end of said root means;

means to attach said one end of said first transmucosal sections to said gingival end of said root means via said attaching means;

a plurality of transfer components for making a model of said site faithfully replicating said opening, said gingival end of said root means and said attaching means, each of said components being attachable at one end to said gingival end of said root means and having a second transmucosal section, a supragingival section adapted for embedment in resilient modelling material, said second transmucosal section of said plurality of transfer components having different sizes which are substantially identical and corresponding to said first transmucosal sections of said plurality healing members; and means to connect said second transmucosal section to said attaching means of said root means through said opening.

34. A set of components according to claim 33 in which the cross-section of each of said transmucosal sections is substantially round at its end confronting said root means and said cross-section gradually changes to non-round as it proceeds away from said one end attachable to said gingival end of said root means.

35. A set of components according to claim 33 in which the cross-sectional shape of each of said transmucosal sections is approximately round.

36. A set of components according to claim 33 including means to lock said healing member members against turning on said root means, and means to lock said transfer component against turning on said root means.

37. A set of components according to claim 33 wherein at least one of said transfer components comprises an elongated body having said transmucosal section at said first end and said supragingival section at a second end, and a through bore between said ends for passage of bolt means to attach said transmucosal section to said root means via said connecting means.

38. A set of components according to claim 37 in which a cross-sectional dimension of said transmucosal section is substantially larger than any cross-sectional dimension of said supragingival section.

39. A set of components according to claim 38 in which said transmucosal section and said supragingival section are separated by an intermediate waist section having transverse dimensions that are smaller than any of said cross-sectional dimensions of said transmucosal and supragingival sections.

40. A set of dental components for use in preparing an artificial tooth for attachment to a dental implant fixed in a jawbone site accessed through a gingiva opening, said set comprising:

multiple healing components selectively attachable to the dental implant, said healing components having different transverse dimensions for forming the gingiva opening to a selected transverse dimension; and multiple transfer components selectively attachable to the dental implant, said transfer components having different transverse dimensions corresponding respectively to the different transverse dimensions of the multiple healing components.

41. The set of dental components as set forth in claim 40 further including at least one restoration component attachable to the dental implant and having a transverse dimension smaller than the transverse dimension of the selected healing component and the corresponding selected transfer component, to allow space between the restoration component and the wall of the gingiva opening.

42. The set of dental components as set forth in claim 40 wherein said transfer components are impression copings for forming models of the gingiva openings with the selected transverse dimensions.

43. The set of dental components as set forth in claim 40 wherein said healing components and said transfer components have transmucosal portions with transverse cross-sections tapering outwardly away from the gingival end of said implant.

44. The set of dental components as set forth in claim 40 wherein said healing components and transfer components have non-round transverse cross-sections.

45. The set of dental components as set forth in claim 40 wherein said implant and said transfer components have mating ends forming cooperating anti-rotational surfaces.

46. A method of fabricating an artificial tooth for attachment to a dental implant fixed in a jawbone site accessed through a gingiva opening, said method comprising selecting a healing component from a set of multiple healing components attachable to the dental implant and having different transverse dimensions, the selected healing component having a transverse dimension corresponding substantially to the transverse dimension, within the gingiva opening, of the natural tooth being replaced, attaching the selected healing component to the implant and allowing the gingiva to heal to said transverse dimension, removing the selected healing component from the implant after the gingiva has healed, selecting a transfer component from a set of multiple transfer components attachable to the dental implant and having different transverse dimensions corresponding to the different transverse dimensions of the multiple healing components, the selected transfer component having a transverse dimension corresponding to that of the selected healing component, attaching the selected transfer component to the implant in the healed gingiva opening, and preparing an artificial tooth having a transverse dimension corresponding to that of the natural tooth being replaced.

47. The method of claim 46 which includes the step of using the selected transfer component to form a model of the gingiva opening having a transverse dimension corresponding substantially to that of the natural tooth being replaced.

48. The method of claim 46 wherein said artificial tooth is prepared on a restoration component attachable to the dental implant and having a transverse dimension at a location within the gingival opening spaced from the implant that is smaller than the transverse dimension at that location of the selected healing component, to allow space between the restoration component and the wall of the gingiva opening for an artificial tooth having a natural emergence profile to be fitted into the gingiva opening.

49. The method of claim 46 wherein said transfer components are impression copings for forming models of the gingiva openings with the selected transverse dimensions.

50. The method of claim 46 wherein said healing component and said transfer component have transmucosal portions with a transverse cross-section tapering outwardly from the gingival end of said implant to approximately the mesial-distal dimension of said natural tooth.

51. The method of claim 46 wherein said healing component and said transfer component have transmucosal portions with a transverse cross-section replicating the emergence profile of said natural tooth.

52. The method of claim 46 wherein said implant and said transfer components have mating ends forming cooperating anti-rotational surfaces.

53. A method of fabricating an artificial tooth for attachment to a dental implant fixed in a jawbone site accessed through a gingiva opening, said method comprising attaching a healing component to the implant and allowing the gingiva to heal to the shape of the healing component, the healing component having a transverse dimension corresponding substantially to the transverse dimension, within the gingiva opening, of the natural tooth being replaced, removing the healing component from the implant after the gingiva has healed, and attaching a transfer coping to the implant within the healed gingiva opening, the transfer coping having a transverse dimension corresponding to that of the healing component and sitting in said opening, making an impression of the gingiva area surrounding the attached transfer coping, making a model from the impression with the transfer coping in the impression and thereby replicating in the model the gingiva opening formed by the healing component, selecting a core abutment which is attachable to the implant and which has a transverse dimension smaller than that of the selected healing component and transfer coping, and forming an artificial tooth on said core abutment, said artificial tooth being dimensioned to extend into the space between said core abutment and the wall of said replicated opening to form a natural emergence profile when said core abutment with said tooth formed on it is mounted on said model within said replicated opening.

54. The method of claim 53 wherein said artificial tooth is prepared on a restoration component attachable to the dental implant and having a transverse dimension at a location within the gingival opening spaced from the implant that is smaller than the transverse dimension at that location of said healing component, to allow space between the restoration component and the wall of the gingiva opening for an artificial tooth having a natural emergence profile to be fitted into the gingiva opening.

55. The method of claim 53 wherein said healing component and said transfer coping have transmucosal portions with a transverse cross-section tapering outwardly from the gingival end of said implant to approximately the mesial-distal dimension of said natural tooth.

56. The method of claim 53 wherein said healing component and said transfer coping have transmucosal portions with a transverse cross-section replicating the emergence profile of said natural tooth.

57. The method of claim 53 wherein said implant and said transfer coping have mating ends forming cooperating anti-rotational surfaces.

58. A transfer component for use in fabricating an artificial tooth to replace a natural tooth to be installed in a jawbone site containing an artificial root means with an overlying gingiva layer having an opening to the root means, said root means having transverse dimensions, in the vicinity of the interface between said jawbone and said gingiva, which are smaller than the transverse dimensions of the natural tooth removed from said site where said tooth emerged from said gingiva, said transfer component comprising;

a non-round transmucosal portion having a first transverse dimension substantially wider than said transverse dimension of said artificial root means for forming said opening into a non-round shape and a lower end for engaging said artificial root means through said gingiva opening, and means for fastening said transfer component to said artificial root means.

59. The transfer component of claim 58, wherein said transmucosal portion have regions which are nearly straight.

60. The set of transfer components according to claim 58 wherein at least one of said set of transfer components is a transfer coping.

61. The set of transfer components according to claim 58 wherein at least one of said set of transfer components is a pick-up coping.

62. A set of dental components for use in preparing a dental restoration to be supported on artificial root means fixed in living bone in a site with an overlying gingiva layer having an opening to the root means, said root means having transverse dimensions, in the vicinity of the interface between said bone and said gingiva, which are substantially smaller than the transverse dimensions of a natural tooth in said site where said tooth emerged from said gingiva, said set comprising:

a non-round healing member which includes a distal portion having generally the diameter of the root means and a proximal portion having a larger diameter for forming said gingiva opening into a size and contour;

means for attaching said healing member to said root means;

a non-round transfer component having substantially the same size and contour as said healing member so as to fit substantially fully into said gingiva opening in place of said healing member; and means for attaching said transfer component to said root means.

63. The set of dental components as set forth in claim 62 which includes a restoration component attachable to the dental implant and having a transverse dimension smaller than the transverse dimension of said healing member, to allow space between the restoration component and the wall of the gingiva opening.

64. The set of dental components as set forth in claim 62 wherein said transfer component is a transfer coping for forming a model of the gingiva opening.

65. The set of dental components as set forth in claim 62 wherein said healing member and said transfer component have transmucosal portions with a transverse cross-section that increase in area when moving away from the gingival end of said implant.

66. The set of dental components as set forth in claim 62 wherein said transfer component is a pick-up coping.

67. The set of dental components as set forth in claim 62 wherein said implant and said transfer component have mating ends forming cooperating anti-rotational surfaces.

68. A method of preparing a dental restoration for installation on artificial root means fixed in living jawbone in a site with an overlying gingiva layer having an opening to the root means, said root means having transverse dimensions, in the vicinity of the interface between said bone and said gingiva, which are substantially smaller than the transverse dimensions of a natural tooth in said site where said tooth emerged from said gingiva, said method comprising the steps of preparing in said gingiva overlying said root means an opening to the gingival aspect of said root means, said opening having at the gingival surface substantially the full cross-sectional size of a natural tooth emerging through said gingiva at said site, furnishing a solid material substantially replicating physical properties of bone overlaid with soft material substantially replicating physical properties of gingiva, forming in said soft material an opening replicating said gingiva opening and forming in said solid material a replica of said gingival aspect of said root means, and forming on said replica of said root means an artificial tooth replicating in said opening in said soft material the emergence shape and contours of said natural tooth, and installing said artificial tooth on said root means.

69. A method of preparing a dental restoration for installation on artificial root means fixed in living jawbone in a site with an overlying gingiva layer having an opening to the root means, said root means having transverse dimensions, in the vicinity of the interface between said bone and said gingiva, which are smaller than the transverse dimensions of a natural tooth in said site where said tooth emerged from said gingiva, said method comprising the steps of preparing in said gingiva overlying said root means an opening to the gingival aspect of said root means, said opening having at the gingival surface substantially the full cross-sectional size of a natural tooth emerging through said gingiva at said site, furnishing a transfer coping having a transmucosal portion with a transverse dimension which substantially replicates the width of said natural tooth at said site where said natural tooth emerged from said gingiva, for engaging to said root means through said opening, and an impression portion adjacent to said transmucosal portion for extending into impression material, fastening said transmucosal portion to said root means, making an impression of said site with said transfer coping attached to said root means, making a model of said site from said impression with said transfer coping attached to said impression, fabricating a restoration on said model substantially to the shape and contours of said natural tooth, and installing said restoration on said root means with said restoration substantially filling said opening at said gingival surface.

70. The method of claim 69 wherein said restoration is prepared on a restoration component attachable to the dental implant and having a transverse dimension at a location within the gingival opening spaced from the implant that is smaller than the transverse dimension at that location, to allow space between the restoration component and the wall of the gingiva opening for a restoration having a natural emergence profile to be fitted into the gingiva opening.

71. The method of claim 69 wherein said transfer coping having a transmucosal portion with a transverse cross-section tapering outwardly from the gingival end of said implant to approximately the mesial-distal dimension of said natural tooth.

72. The method of claim 69 wherein said transfer coping having a transmucosal portion with a transverse cross-section replicating the emergence profile of said natural tooth.

73. The method of claim 69 wherein said implant and said transfer coping have mating ends forming cooperating anti-rotational surfaces.

74. A method of preparing a dental restoration for installation on root means fixed in living jawbone in a site with an overlying gingiva layer having an opening to the root means, said root means having transverse dimensions, in the vicinity of the interface between said bone and said gingiva, which are substantially smaller than the transverse dimensions of a natural tooth in said site where said tooth emerged from said gingiva, said method comprising the steps of preparing in said gingiva overlying said root means an opening to the gingival aspect of said root means, said opening having at the gingival surface substantially the full cross-sectional size of a natural tooth emerging through said gingiva from said root means, selecting a transfer coping having a transmucosal portion with a transverse dimension which replicates the width of said natural tooth at said site where said natural tooth emerged from said gingiva, for engaging to said root means through said opening, and an impression portion adjacent to said transmucosal portion for extending into impression material, fastening said transmucosal portion to said root means, making an impression of said site with said transfer coping attached to said root means, making a model of said site from said impression with said coping attached to said impression, selecting a core abutment which is attachable to the implant and which has a transverse dimension smaller than said transmucosal portion of said transfer coping, forming a restoration on said core abutment substantially to the shape and contours of said natural tooth and dimensioned to extend into the space between said core abutment and the wall of said gingiva opening to form a natural emergence profile when said core abutment with said restoration formed thereon is mounted on said model within said gingiva opening, and installing said restoration on said root means with said restoration substantially filling said opening at said gingival surface.

75. The method of claim 74 wherein said transfer coping having a transmucosal portion with a transverse cross-section tapering outwardly from the gingival end of said implant to approximately the mesial-distal dimension of said natural tooth.

76. The method of claim 74 wherein said transfer coping having a transmucosal portion with a transverse cross-section replicating the emergence profile of said natural tooth.

77. The method of claim 74 wherein said implant and said transfer components have mating ends forming cooperating anti-rotational surfaces.

78. A set of dental components for use in preparing a dental restoration to be supported on artificial root means fixed in living bone in a site with an overlying gingiva layer having an opening to the artificial root means, said artificial root means having a transverse dimension in the vicinity of the interface between said bone and said gingiva, which is substantially smaller than the transverse dimension of the natural tooth removed from said site, where said tooth emerged from said gingiva, said set of dental components comprising:

multiple healing components each having a transmucosal portion with a transverse dimension for forming said opening to approximately the size of said transverse dimension;

means for attaching one of said healing members to said artificial root means;

multiple transfer components each having a transmucosal portion with substantially the same transverse dimension as a corresponding one of said healing components so as to fit substantially fully into said gingiva opening in place of said corresponding healing member, at least the transmucosal portion of one of said transfer components having a different contour than the remaining ones of said transfer components; and means for attaching one of said transfer components to said artificial root means with said transmucosal portion fitted into said gingiva opening.

79. The set of dental components as set forth in claim 78 which includes at least one restoration component attachable to the dental implant and having a transverse dimension at a location within the gingival opening spaced from the implant that is smaller than the transverse dimension at that location of said healing component, to allow space between the restoration component and the wall of the gingiva opening.

80. The set of dental components as set forth in claim 78 wherein said transfer coping is an impression coping for forming a model of the gingiva opening with the desired transverse dimension.

81. The set of dental components as set forth in claim 78 wherein said healing components and said transfer components have transmucosal portions with a transverse cross-section tapering outwardly from the gingival end of said implant.

82. The set of dental components as set forth in claim 78 wherein said healing components and said transfer components have transmucosal portions with a non-round transverse cross-section.

83. The set of dental components as set forth in claim 78 wherein said implant and said transfer coping have mating ends forming cooperating anti-rotational surfaces.

84. The set of dental components of claim 78, wherein at least one of said transfer components is a transfer coping.

85. The set of dental components of claim 78, wherein at least one of said transfer components is a pick-up coping.

* * * * *

UNITED STATES PATENT AND TRADEMARK OFFICE
CERTIFICATE OF CORRECTION

PATENT NO. : 5,674,071

DATED : October 7, 1997

INVENTOR(S) : Beaty et al.

It is certified that error appears in the above-identified patent and that said Letters Patent is hereby corrected as shown below:

Claim 2, column 6, line 49, delete "layer";

Claim 3, column 6, line 54, delete "layer";

Claim 4, column 6, line 58, change ", having" to --and has-- therefor;

Claim 4, column 6, line 58, delete "having" (second occurrence);

Claim 7, column 7, line 18, delete "diameter";

Claim 7, column 7, line 21, change "and" to --from-- therefor;

Claim 7, column 7, line 22, delete "dimensions";

Claim 7, column 7, line 26, change "replicating in" to --,-- therefor;

Claim 7, column 7, line 27, after "model" insert --replicating--;

Claim 12, column 8, line 45, after " portion;" insert --and--;

Claim 13, column 8, line 52, after "one" insert --of--;

Claim 19, column 9, line 47, after "larger sections of said plurality" insert --of--;

Claim 22, column 9, line 59, after "a" delete "natural or artificial";

Claim 22, column 9, line 61, change "said root means" to --said root-- therefor;

UNITED STATES PATENT AND TRADEMARK OFFICE
CERTIFICATE OF CORRECTION

PATENT NO.    :   5,674,071

DATED         :   October 7, 1997

INVENTOR(S)   :   Beaty et al.

It is certified that error appears in the above-identified patent and that said Letters Patent is hereby corrected as shown below:

Claim 22, column 9, lines 61-62 change "gingival end" to --gingival aspect-- therefor;

Claim 33, column 11, line 39, after "sections of said plurality" insert --of--;

Claim 36, column 11, line 54, delete "member";

Claim 59, column 14, line 35, change "have" to --has-- therefor;

Claim 62, column 14, line 54, after "contour" insert --at said site--;

Claim 68, column 15, line 24, at the end of the line after "of" insert a --:--;

Claim 69, column 15, line 47, at the end of the line after "of" insert a --:-- therefor; and Claim 74, column 16, line 31, at the end of the line after "of" insert a --:--.

Signed and Sealed this

Twenty-eighth Day of July, 1998

Attest:

BRUCE LEHMAN

*Attesting Officer*     *Commissioner of Patents and Trademarks*